United States Patent [19]

Mistretta

[11] 4,204,225

[45] May 20, 1980

[54] REAL-TIME DIGITAL X-RAY SUBTRACTION IMAGING

[75] Inventor: Charles A. Mistretta, Madison, Wis.

[73] Assignee: Wisconsin Alumni Research Foundation, Madison, Wis.

[21] Appl. No.: 960,830

[22] Filed: Nov. 15, 1978

Related U.S. Application Data

[63] Continuation-in-part of Ser. No. 906,686, May 16, 1978, abandoned.

[51] Int. Cl.² ............................................. H04N 5/32
[52] U.S. Cl. ............................ 358/111; 250/416 TV; 128/695
[58] Field of Search ......................... 358/111, 96, 166; 250/416 TV, 272, 320, 321; 128/2 A

[56] References Cited

U.S. PATENT DOCUMENTS

| | | | |
|---|---|---|---|
| 3,668,396 | 6/1972 | Asars et al. ................... | 250/416 TV |
| 3,854,049 | 12/1974 | Mistretta et al. ................... | 250/402 |
| 3,894,181 | 7/1975 | Mistretta et al. ................... | 358/111 |
| 3,974,386 | 8/1976 | Mistretta et al. ................... | 250/402 |
| 4,125,858 | 11/1978 | Hounsfield et al. ................. | 358/111 |

FOREIGN PATENT DOCUMENTS 2539870  9/1976  Fed. Rep. of Germany ... 250/416 TV

OTHER PUBLICATIONS

Gilbert et al., "A Real-Time Hardware System for Digital Processing of Wide Band Video Images", IEEE Trans. on Computers, vol. C25, No. 11, 11–76, pp. 1089–1100.
Brennecke, "A Digital System for Roentgen Video Image Processing", 2nd International Workshop Conference, 4–76, pp. 151–157.
Bailey et al., "Capabilities of a Single Scan TV Radiographic System for Digital Data Acquisition Investigative Radiology", 7-8/71, pp. 273–279.
Bailey et al., "Fluoroscopic Tomography", pp. 94–103, Investigative Radiology, vol. 9, #2, Mar.–Apr. 1974.
Robb et al., "Three-Dimensional Reconstruction and Display of the Heart, Lungs and Circulation by Multiplanar X-Ray Scanning Video Densitometry Cardiovascular Imaging and Imaging Processing", SPIE Publ., pp. 183–194.

Primary Examiner—Robert L. Griffin
Assistant Examiner—Edward L. Coles
Attorney, Agent, or Firm—Burmeister, York, Palmatier, Hamby & Jones

[57] ABSTRACT

Difference images, derived from an X-ray image of an anatomical subject, are produced in real time by directing X-rays through the anatomical subject to produce an X-ray image, converting the X-ray image into television fields comprising trains of analog video signals, converting the analog video signals into digital video signals, producing integrated mask digital video signals by integrating the digital video signals over a mask time interval, subtracting the integrated mask digital video signals from corresponding digital video signals of television fields subsequent to the mask time interval and thereby producing digital difference video signals, converting the digital difference video signals into analog difference video signals, and converting the analog difference video signals into a series of visible television difference images representing changes in the X-ray image subsequent to the mask time interval. The mask time interval preferably corresponds generally to at least one complete cardiac cycle of the anatomical subject. An X-ray contrast medium is preferably injected into a peripheral blood vessel of the anatomical subject, with a timing such that the contrast medium appears in the X-ray image subsequent to the mask time interval. In another embodiment, the integrated mask digital video signals are reconverted to analog form and are subtracted on an analog basis from the analog video signals produced subsequent to the mask time interval, to produce the analog difference video signals.

65 Claims, 5 Drawing Figures

| TV FIELDS | FUNCTIONS | | | DIFFERENCE IMAGE |
|---|---|---|---|---|
| | MEMORY 1 | MEMORY 2 | MEMORY 3 | |
| MASK INTERVAL (e.g. 1-31) | INTEGRATE | — | — | — |
| IMAGE 1 (e.g. 32-35) | RECIRCULATE | INTEGRATE | — | — |
| IMAGE 2 (e.g. 36-39) | OUTPUT: SUBTRACT | OUTPUT: ADD | INTEGRATE | IMAGE 1 minus MASK |
| IMAGE 3 (e.g. 40-43) | " | INTEGRATE | OUTPUT: ADD | IMAGE 2 minus MASK |
| IMAGE 4 (e.g. 44-47) | " | OUTPUT: ADD | INTEGRATE | IMAGE 3 minus MASK |
| IMAGE 5 (e.g. 48-51) | " | INTEGRATE | OUTPUT: ADD | IMAGE 4 minus MASK |

REAL-TIME DIGITAL X-RAY SUBTRACTION IMAGING

The Government has rights in this invention pursuant to Grant No. APR 76-19076 and IPA No. 0001 awarded by the National Science Foundation.

This application is a continuation-in-part of applicant's copending application, Ser. No. 906,686, filed May 16, 1978, now abandoned.

This invention relates to real-time digital X-ray subtraction imaging methods and apparatus, which will find many applications in making diagnostic X-ray studies of humans and animals, but are particularly well adapted for visualizing the cardiovascular system, including the heart and any blood vessels which are of interest. This invention is able to produce a series of continuous television images, showing the circulation of the blood in any desired portion of the cardiovascular system. Thus, the present invention is extremely valuable for visualizing the motion of the heart in real time, and for showing the circulation of the blood in the arteries and veins which are associated with the heart. This invention is also very advantageous for making X-ray studies of the abdomen and the brain. For example, the present invention may be employed very advantageously for showing the circulation of the blood in the renal arteries and veins, associated with the kidneys, and in the carotid arteries and veins, in the neck and head.

One object of the present invention is to produce television difference images, in which the circulating blood is shown with greatly enhanced visibility, while image elements due to bone and soft tissue are largely eliminated by subtraction.

A further object is to produce television difference images in which the visibility of an X-ray contrast medium is enhanced to such a great extent that the contrast medium can be injected into one or more peripheral veins in the arms or legs of the patient, without any need to insert a catheter, as in prior procedures.

Another object is to produce television different images whereby the circulating blood is visualized to a useful extent, without utilizing any contrast medium.

Generally, the present invention provides a method of producing visible difference images derived from an X-ray image of an anatomical subject, comprising the steps of directing X-rays through the anatomical subject for producing an X-ray image, converting the X-ray image into television fields comprising trains of analog video signals, converting the analog video signals into digital video signals, producing integrated digital video signals by integrating the digital video signals over a predetermined time interval corresponding to a plurality of television fields, producing digital difference video signals by performing a subtraction between the ongoing video signals and the corresponding integrated digital video signals, converting the digital difference video signals into analog difference video signals, and converting the analog difference video signals into visible television difference images representing changes in the X-ray image.

One embodiment, called the mask mode, involves producing integrated mask digital video signals by integrating the digital video signals over a predetermined number of television fields for a mask time interval, and subtracting the integrated mask digital video signals from corresponding digital video signals of television fields subsequent to the mask time interval, and thereby producing digital difference video signals, which are converted into visible television difference images, as before. In the mask mode, it is preferred to introduce an X-ray contrast medium into the subject, with a timing such that the contrast medium is not operative during the mask time interval, but becomes operative during the production of the television difference images. The subtraction of the integrated mask video signals greatly enhances the visibility of the contrast medium.

The apparatus for carrying out the mask mode preferably includes a first digital memory system for storing and integrating the digital mask video signals over the mask time interval, second and third memory systems for integrating the ongoing video signals over shorter intervals corresponding to a few television fields, and subtracting means for producing digital difference video signals by performing a series of subtractions in which the integrated mask digital video signals are subtracted alternately from the integrated video signals produced by the second and third memory systems.

The mask time interval preferably corresponds generally with at least one complete cardiac cycle of the anatomical subject, or a major fraction of one complete cardiac cycle. Unexpectedly, this mask time interval has been found to be highly advantageous.

In a modified embodiment of the mask mode, the digital integrated mask video signals are reconverted to analog form and are subtracted on an analog basis from the analog video signals produced subsequent to the mask time interval, to produce the analog difference video signals, which are displayed as television difference images. This modified embodiment requires only one memory system, to store and integrate the video signals during the mask time interval, so as to produce the integrated mask video signals. The ongoing video signals and the video difference signals are handled in a purely analog channel, so that the full resolution or fidelity of the analog channel is available to process the video signals. In this modified embodiment, no electronic integration is provided for the ongoing video signals or the video difference signals, but a type of integration may be produced by providing a motion picture camera to photograph the television difference images. The motion picture camera may be synchronized with the television monitor, in such a manner that a plurality of successive television fields are photographed on each frame produced by the motion picture camera.

Further objects, advantages and features of the present invention will appear from the following description, taken with the accompanying drawings, in which.

Figure 1:
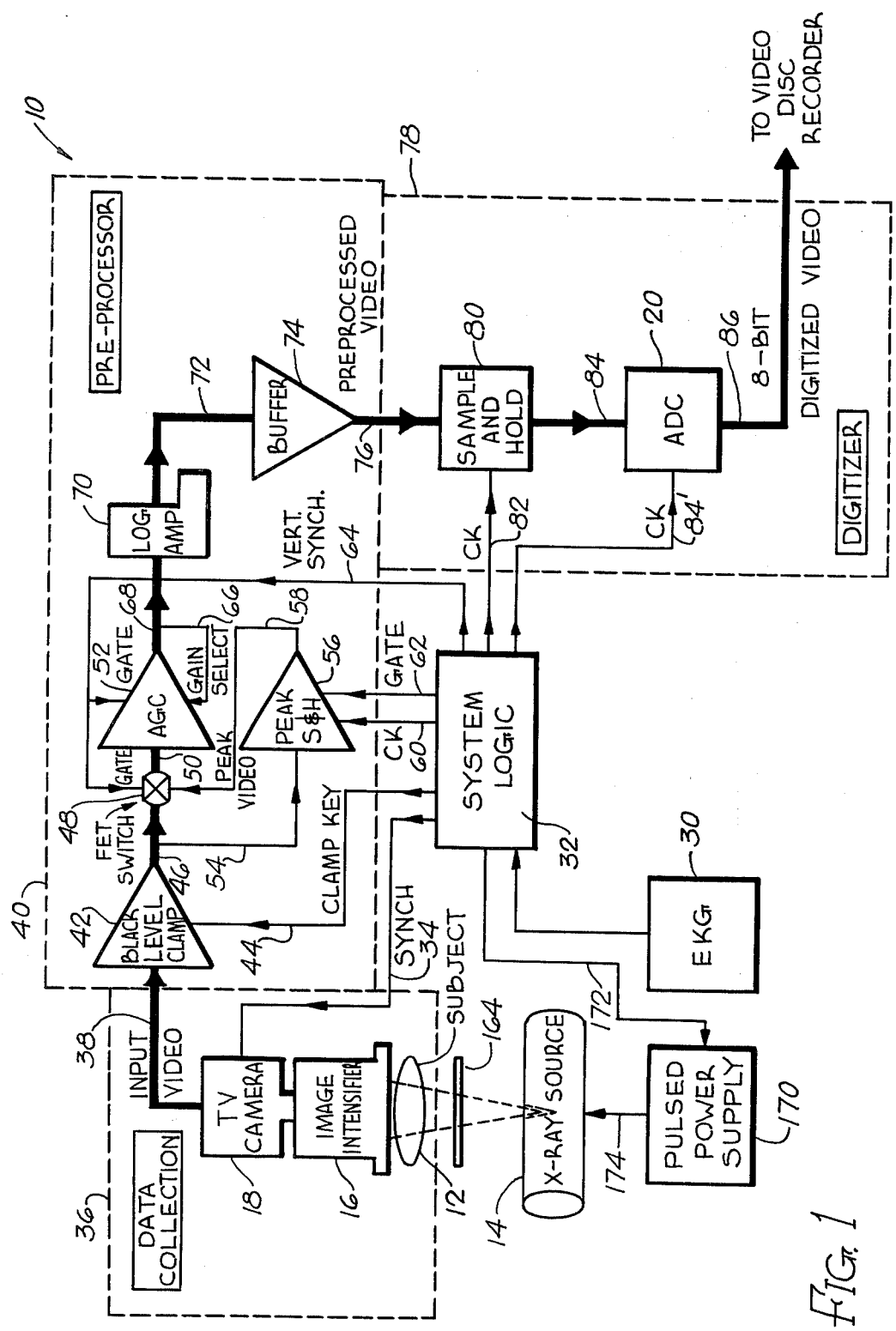
FIG. 1 is a schematic block diagram of X-ray apparatus illustrating the production of digital video signals corresponding with an X-ray image of a subject or patient.
Figure 2:
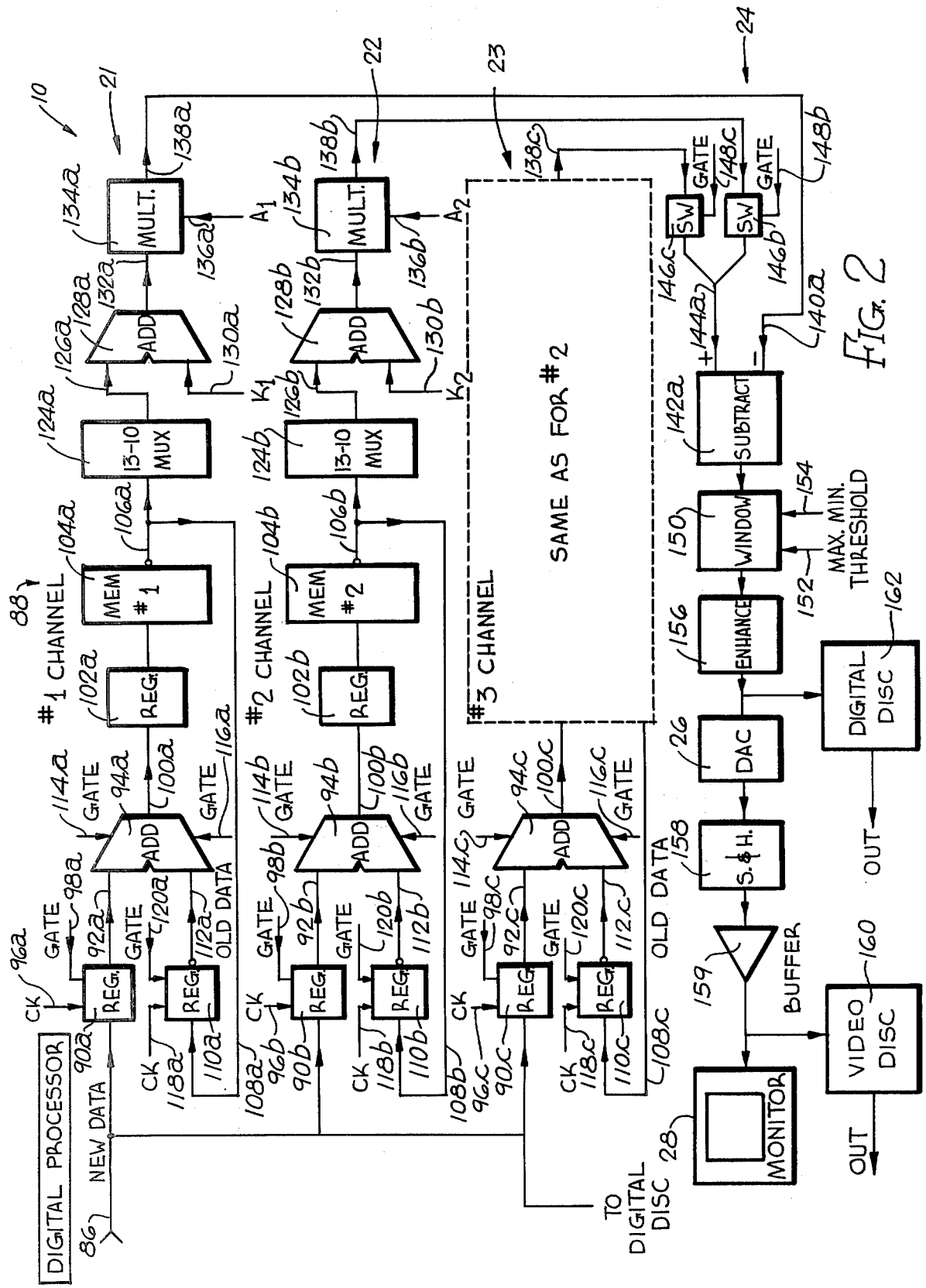
FIG. 2 is a schematic block diagram of apparatus illustrating the production of television difference images from the digital video signals, in accordance with the mask mode.
Figures 3, 4:
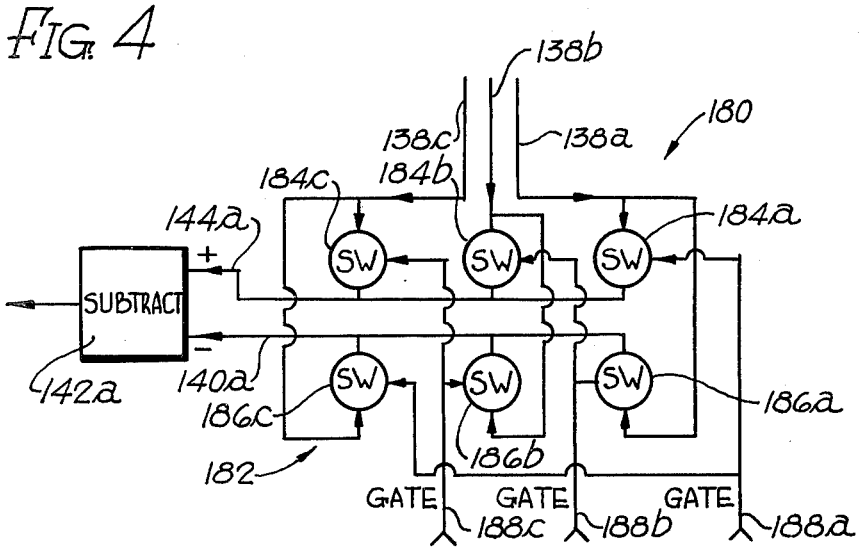
FIG. 3 is a table illustrating details of the construction and operation of the apparatus of FIGS. 1 and 2.
FIG. 4 is a schematic block diagram of modified apparatus embodying the generic invention.

FIGS. 1–3 illustrate an embodiment of the present invention in the form of diagnostic anatomical X-ray apparatus 10 which will find many applications, but is particularly well adapted for producing a continuous series of images in real time to show any desired portion of the cardiovascular system of a patient or subject 12. Thus, for example, the X-ray apparatus 10 may be employed for visualizing the heart, with its associated arteries and veins, the various abdominal organs with the associated blood vessels, or the brain, with its associated arteries and veins.

The X-ray apparatus 10 is particularly well adapted for producing a continuous series of images in real time to show the motion of the heart. In carrying out such studies of the heart and other portions of the cardiovascular system, it generally is desirable to introduce an X-ray contrast medium, such as a composition containing iodine, into the cardiovascular system of the subject 12. However, the X-ray apparatus 10 is so sensitive that the contrast medium can be injected peripherally, into one or more peripheral veins in an arm or leg of the subject 12. There is no need for using a catheter, as in certain prior procedures, to introduce the contrast medium into a localized zone of the cardiovascular system. In one such prior procedure, it has been the practice to insert the cathether through an incision into a blood vessel to a location close to the heart, so that the contrast medium can be supplied through the catheter, directly to the heart. The use of a catheter results in a high concentration of the contrast medium in the heart. However, this procedure involves a significant hazard of producing an adverse reaction in the patient. It is much less hazardous to inject the contrast medium into a peripheral vein, without the use of a catheter. The X-ray apparatus of the present invention is capable of effectively visualizing the motion of the heart, with peripheral injection of the X-ray contrast medium, and without any need to use a catheter. Similarly, other portions of the cardiovascular system can be effectively visualized, with peripheral injection of the contrast medium, and without using a catheter.

The present invention, as represented by FIGS. 1–3, involves a method in which a continuous series of difference images are produced by developing a preinjection mask image, prior to the injection of the contrast medium, and electronically subtracting the mask image from each of a series of post-injection images. This mask subtraction mode results in the substantial cancellation of image elements due to bone and soft tissue, so that the image elements due to the contrast medium can be visualized with high contrast.

Preferably, the diagnostic anatomical X-ray apparatus 10 of FIGS. 1–3 comprises means including an X-ray source or generator 14 for producing an anatomical X-ray image of the subject 12, means including an image intensifier device 16 for producing a visible anatomical image corresponding with the X-ray image, television means including a television camera 18 for converting the visible image into a continuous series of television fields comprising trains of analog video signals, an analog-to-digital converter 20 for converting the analog video signals into corresponding digital video signals, means including a mask producing memory system 21 (FIG. 2) for storing and integrating the digital video signals over a predetermined mask time interval, generally corresponding with a predetermined number of television fields, subtracting means 24 for producing digital difference video signals by performing a subtraction between the digital video signals subsequent to the mask time interval and the corresponding integrated digital video signals stored in the mask memory system, a digital-to-analog converter 27 for converting the digital difference video signals into analog difference video signals, and means including a television display device 28 for producing visible difference images corresponding to the analog difference video signals and representing changes in the anatomical X-ray image taking place subsequent to the mask time interval. Generally, the X-ray contrast medium is injected into the subject with a timing such that the contrast medium is not operative during the mask time interval, but becomes operative subsequent to the mask time interval, so that the contrast medium is visualized in the difference images.

In addition to the first memory system 21, which integrates and stores the mask video signals, the X-ray apparatus 10 also preferably includes second and third digital memory systems 22 and 23 for integrating and temporarily storing the digital video signals for a continuous series of shorter time intervals, subsequent to the mask time interval. For example, the second and third memory systems 22 and 23 may alternately integrate the subsequent digital video signals over time intervals on the order of four television fields, which has the important advantage of greatly improving the signal-to-noise ratio of the digital video signals. The integrated mask video signals from the first memoery system 21 are subtracted alternately by the subtracting means 24 from the integrated subsequent video signals from the second and third memory systems 22 and 23. The provision of the two additional memory systems 22 and 23 makes it possible to produce a continuous television display on the television display device or monitor 28. While one of the memory systems 22 and 23 is integrating the digital video signals over the desired time interval, such as four television fields, the other memory system is providing an output of previously integrated digital video signals to the subtracting means 24. The second and third memory systems 22 and 23 alternately assume the functions of integrating the new digital video signals and providing an output of previously integrated video signals, from which the mask video signals from the first memory system 21 are subtracted. The resulting digital difference video signals are thus supplied continuously to the digital-to-analog converter 26 which provides corresponding analog difference video signals for display by the television display device 28.

The mask time interval, during which the first memory system 21 integrates the pre-contrast digital video signals, is generally substantially longer in duration than the integrating time intervals of the second and third memory systems. It is generally advantageous to establish the mask time interval so that it is comparable, at least roughly, to one complete cardiac cycle of the subject or patient 12. The integrated mask image is thus averaged over the cardiac cycle. This has the effect of blurring the heart motion in the mask image.

In one method, the mask time interval is assigned a predetermined value, such as approximately one half second, which roughly corresponds with one complete cardiac cycle. It has been found that the mask time interval may be established at 31 television fields with good results, on the basis of a television field frequency of 60 television fields per second.

An alternative method is to provide a source 30 (FIG. 1) of electrocardiographic signals, which are employed to synchronize the mask time interval, at least roughly, with one complete cardiac cycle of the subject. It will be understood, however, that the mask time interval should preferably be made equal to a whole number of television fields.

As previously indicated, the integrating intervals of the second and third memory systems 22 and 23 are generally equal to only a few television fields. For example, if each integrating interval is made equal to four television fields, the X-ray system 10 will produce fifteen complete difference images per second, based on a television field frequency of 60 Hertz. Generally, the image resolution of the heart motion will suffer if the integrating interval of the second and third memory systems 22 and 23 is made much greater than four television fields. On the other hand, the signal-to-noise ratio will suffer if the integrating interval is made less than four television fields.

Additional details of the X-ray system 10 are shown in FIGS. 1-3. The entire system is controlled by system logic or control means 32, which provides all of the control, timing and synchronizing pulses and signals for the entire system 10. Thus, the system logic 32 provides both horizontal and vertical synchronizing pulses for the television camera 18, as represented by a control line 34. The television synchronizing pulses are also provided for all other components of the television system, as needed.

The image intensifier 16 and the TV camera 18 constitute data collection means 36, from which analog video signals are delivered along a signal line 38, extending to a preprocessor 40, which amplifies and processes the analog video signals. Initially, the analog video signals are transmitted through a black level clamp circuit 42, which clamps the black level of the television signals to ground or zero voltage. Clamp key pulses are supplied to the black level clamp circuit 42 from the system logic 32 along a line 44, to synchronize the operation of the black level clamp circuit 42 with the television fields.

The analog video signals are then transmitted along a line 46 to an F.E.T. switch 48, or any other suitable electronic switch, which selectively supplies the analog video signals along a line 50 to an automatic gain control circuit 52. The analog video signals from the black level clamp circuit are also supplied along a line 54 to a peak sample and hold circuit 56 which is involved in the operation of the automatic gain control circuit 52. The output of the circuit 56 is supplied along a line 58 to a second input of the electronic switch 48. The peak sample and hold circuit 56 is supplied with clock pulses and gate or control pulses by the system logic 32, over lines 60 and 62, whereby the operation of the circuit 56 is synchronized with the television fields. The system logic 32 also supplies vertical synch pulses along a line 64 to the automatic gain control circuit 52 and the electronic switch 48.

During each television field, the peak sample and hold circuit 56 samples and holds the peak video signal, and thus delivers the peak video signal to the line 58. During the vertical retrace between the television fields, the corresponding vertical synch pulse gates the switch 48, so that the input of the automatic gain control circuit is disconnected from the normal video line 46 and is connected to the peak video line 58. Thus, the peak video output of the circuit 56 is applied to the input of the automatic gain control circuit 52. At the same time, the automatic gain control circuit 52 is gated into its adjust mode by the vertical synch pulse, so that the output of the automatic gain control circuit is adjusted to a preselected desirable level. The output is fed back into the automatic gain control circuit 52 along a gain select line 66. With this circuit operation, the peak video signal for each television field selects the gain for the next television field.

The analog video signals from the automatic gain control circuit 52 are supplied along a line 68 to the input of a logarithmic amplifier 70, adapted to provide amplified output video signals which are proportional to the lagarithm of the input video signal. It has been found that the provision of logarithmic amplification makes it possible to cancel out the background bone and soft tissue elements of the image when the mask image is subtracted from the subsequent images.

In this case, the output of the logarithmic amplifier 70 is supplied along a line 72 to a buffer amplifier 74, which provides amplified output signals to an output line 76, at a sufficiently high level for effective processing by a digitizer circuit 78.

As shown, the digitizer circuit 78 includes a sample and hold circuit 80 which receives the amplified analog video signals from the output line 76 of the buffer amplifier 74. The system logic 32 supplies clock pulses along a line 82 to the sample and hold circuit 80. The output of the sample and hold circuit 80 is supplied along a signal line 84 to the analog-to-digital converter (ADC) 20. The system logic 32 supplies clock pulses to the ADC 20 along a control line 84'. The ADC 20 converts the analog video signals into digital video signals, which are supplied to an output line 86. The digital output may be in the form of eight-bit digital signals, or in any other suitable form.

The sample and hold circuit 80 samples the analog video signals periodically, as determined by the clock pulses from the line 82, and holds the sampled analog value without change until the next clock pulse comes along. When the analog signal has been sampled and is being held, the sampled signal is digitized by the ADC 20. This circuit arrangement has the advantage that each sampled analog value is held constant while it is being digitized by the ADC 20, so that the analog value does not change during the digitizing process. This feature makes it possible to digitize the analog video signals with a greater degree of accuracy.

The digital video line 86 also appears in FIG. 2, which illustrates digital processor circuits 88 for integrating, storing and subtracting the digital video signals, to provide digital difference video signals. As previously indicated, the circuits 88 preferably include the first, second and third memory systems or channels 21, 22 and 23. The digital video signals on the line 86 are supplied to the inputs of all three memory systems 21, 22 and 23, which are timed and controlled by pulses from the system logic control means 32.

All three memory systems 21-23 may be the same in construction. Thus, it will be sufficient to describe the first memory system 21 in detail. The digital video input line 86 is connected to the input of a register 90a having its output connected to one input 92a of an addition circuit 94a. Clock and gate or control pulses are supplied to the register 90a by the system logic 32 over clock and gate lines 96a and 98a.

The output of the addition circuit 94a is supplied along a line 100a to the input of a register 102a having its output connected to the input of a digital memory 104a, capable of storing the digital signals for at least one complete television field. While memories having various storage capacities may be employed, good results have been achieved with a digital memory having a storage capacity of 256×256×13. This storage capacity means that the digital memory 104a is capable of storing 13-bit digital words or values for 256 picture elements (pixels) for each of 256 television lines. This storage capacity amounts to 65,536 thirteen-bit digital words or values. The digital words are adapted to be circulated through the memory 104a and to be delivered successively to an output line 106a.

For the purpose of integration, the old data words from the output line 106a are supplied along a line 108a to the input of a register 110a having its output connected to a second input 112a of the addition circuit 94a. When the addition circuit 94a is processing data received from both input lines 96a and 112a, the two sets of data words are additively combined and are supplied to the output line 100a. Thus, the new digital video signals and the old or previously stored digital video signals are additively combined and are supplied to the input of the digital memory 104a for further storage. The additive processing of the data from the two input lines 92a and 112a is controlled by gate or control pulses supplied to the addition circuit 94a by the system logic 32 over gate pulse lines 114a and 116a. The system logic 32 supplies clock and gate or control pulses to the register 110a over clock and gate lines 118a and 120a.

As previously indicated, the first memory system 21 is preferably employed to integrate and store the digital video signals during an initial mask time interval, prior to the introduction of any X-ray contrast medium into the subject 12. This mask time interval generally corresponds with a relatively large number of television fields, such as 31.

On this basis, the gate pulses for the register 90a are timed so that this register transmits the new digital video signals throughout the mask time interval, and then ceases to transmit the digital video signals. The gate pulses for the old data register 110a are timed so that it transmits the old or previously stored digital video signals throughout the mask time interval and continuously after the mask time interval.

The gate pulses for the addition circuit 94a are timed so that it additively combines the digital video signals from both input lines 92a and 112a throughout the mask time interval, and then ceases to accept any input from the new data input line 92a, while continuing to accept and transmit digital video signals from the old data input 112a. The registers 90a and 110a clocked so that they supply the new and old digital video signals with the proper synchronization to the addition circuit 94a.

The register 102a is provided to supply the integrated digital video signals with the proper synchronization to the digital memory 104a, even though the pulses from the addition circuit 94a may deviate slightly from the proper synchronization. During each television field of the mask time interval, the new digital video signals are added to the recirculating, previously stored digital video signals, and the combined or integrated video signals are again fed into the digital memory 104a for storage therein. After the end of the mask time interval, the new digital video signals are no longer added, so that the previously stored digital video signals are simply recirculated through the memory 104a, the register 110a, the addition circuit 94a and the register 102a. During each television field after the mask time interval, the integrated mask video signals appear at the output line 106a of the digital memory 104a and are supplied to the subtraction means 24, after some further processing.

To provide such further processing, the first memory system 21 comprises a thirteen-ten multiplexer 124a which converts or normalizes the thirteen-bit digital words or values from the digital memory 104a into ten-bit digital words or values, incorporating the most significant bits of the 13-bit words. The output line 106a from the digital memory 104a is connected to the input of the 13-10 multiplexer 124a. The ten-bit output words from the multiplexer 124a are supplied to one input 126a of an addition circuit 128a, which is provided for the purpose of adding a variable constant $K_1$ to the 10-bit digital video signals. The system logic 32 supplies the constant $K_1$ to the second input of the addition circuit 128a over a line 130a. The constant $K_1$ is in the form of a ten-bit digital word which can be selected by the operator. If no constant needs to be added, the operator simply enters zero as the constant $K_1$. The ability to add a constant makes it possible to adjust the digital video signals for the best possible subtraction by the subtraction unit 24.

The output of the addition unit 128a is supplied to one input 132a of a multiplication circuit 134a, having a second input 136a which is supplied with a coefficient $A_1$ by the system logic 32. The coefficient $A_1$ is in the form of a digital word which can be selected by the operator. If no multiplication is needed, the coefficient is selected as 1. However, the ability to introduce a coefficient makes it possible to adjust the digital video signals for the best possible subtraction by the subtraction circuit 24. The output 138a of the multiplication unit 134a is supplied to the subtract input line 140a of a subtraction circuit 142a which is a component of the subtraction means 24. In the subtraction circuit 142a, the integrated mask digital video signals at the subtract input 140a are subtracted from new digital video signals, produced subsequent to the mask time interval.

These new digital video signals are preferably integrated and supplied alternately by the second and third memory systems 22 and 23 to the add input 144a of the subtraction circuit 142a.

As previously indicated, the second and third memory systems 22 and 23 may be the same in construction as the first memory system 21. In FIG. 2, the various components of the second and third memory systems have been identified with the same reference characters as employed for the corresponding components of the first memory system 21, with the addition of the suffixes b and c, instead of a. Thus, the second and third memory systems 22 and 23 have output lines 138b and c which are connected alternately to the add input line 144a of the subtraction circuit 142a by electronic switches 146b and c. Gate or control pulses are supplied alternately to the switches 146b and c by the system logic 32 along gate lines 148b and c. Thus, the electronic switches 146b and c are alternately rendered operative to transmit digital video signals from the second and third memory systems 22 and 23, for successive, relatively brief time intervals, generally amounting to a few television fields. As previously indicated, such alternate time intervals are typically on the order of four television fields.

During each interval in which the second memory system 22 is integrating the incoming digital video signals, the new data input register 90b, the old data input register 110b and the addition circuit 94b are switched into fully operative states by their respective gating pulses from the system logic 32. Thus, the newly received digital video signals are added to the old digital video signals, previously stored in the second digital memory 104b. The combined or integrated digital video signals are again stored in the second memory 104b. During this time interval, the electronic switch 146b is rendered inoperative by its gating pulses, so that the output of the second memory system 22 is not supplied to the subtraction circuit 142a. Instead, any previously stored digital video signals at the output 138c of the third memory system 23 are supplied to the subtraction circuit 142a by the electronic switch 146c, which is rendered operative by its gating pulses.

At the end of the brief integrating interval of the second memory system 22, the new data input register 90b is shut down by its gating pulses, so that the newly received digital video signals are no longer added to the integrated digital video signals. Thus, the integrated signals simply continue to circulate through the second memory system 22. The electronic switch 146c is shut down, while electronic switch 146b is rendered operative by the gating pulses, so that the integrated digital video signals from the second memory system 22 are supplied to the add input 144a of the subtraction circuit 142a, instead of the output signals from the third memory system 23. The situation continues for a few television fields, typically four television fields. Meanwhile, the newly received digital video signals are being integrated by the third memory system 23, in the same manner as described in connection with the second memory system 22.

Thus, the second and third memory sytems 22 and 23 alternately perform writing and reading functions during successive brief intervals, on the order of four television fields. The writing function involves integration and storage of the newly received digital video signals. The reading function involves the transmission of the integrated and stored digital video signals to the subtraction circuit 142a.

At its output, the subtraction circuit 142a produces digital difference video signals which may be subjected to additional processing before being supplied to the digital-to-analog converter 26. Thus, in the apparatus of FIG. 2, the output of the subtraction circuit 142a is supplied to the input of a window or threshold circuit 150, which preferably establishes adjustable minimum and maximum thresholds, as determined by adjustable control signals supplied by the system logic 32 to maximum and minimum threshold control lines 152 and 154 connected to the window circuit 150. Thus, all of the digital video signals below the minimum threshold will be rendered or displayed as black, while all of the digital video signals above the maximum threshold will be rendered or displayed as white.

In the apparatus of FIG. 2, the output of the window circuit 150 is connected to the the input of an adjustable enhance circuit 156, which reduces the number of bits in the digital difference video signals and selectively determines whether the bits transmitted to the DA converter 26 will be derived from the lower order or higher order bits of the input signals. For example, the input digital video signals to the enhance circuit 156 may have nineteen bits, while the output signals may have ten bits, to match the desired number of input bits for the DA converter 26. The enhance circuit 156 can be adjusted to slide the selected group of ten bits anywhere along the nineteen bit input scale. If the ten bits of the lowest order are selected, the contrast at the black end of the television scale will be enhanced. If the ten bits of the highest order are selected, the contrast at the white end of the television scale will be enhanced. The presence of nineteen bits at the input to the enhance circuit 156 is due to the multiplication operations in the multiplication circuits 134a, b and c. As previously indicated, the input digital video signals to the multiplication circuits 134a, b and c may contain ten bits. If the coefficients $A_1$, $A_2$ and $A_3$ contain nine bits, the digital output video signals from the multiplication circuits 134a, b and c will contain nineteen bits in each digital word. The numbers of bits are given by way of example and may be varied, as desired.

The digital difference video signals from the output of the enhance circuit 156 are supplied to the input of the digital-to-analog converter 26, which converts the digital difference video signals into analog difference video signals. The analog output of the DA converter 26 is supplied to a sample and hold circuit 158 which removes minor oscillations or transients which are introduced by the DA converter 26. Such oscillations or transients tend to occur at the beginning of each analog signal component corresponding to each digital word which is converted by the DA converter 26. The sample and hold circuit 158 is able to remove such oscillations by sampling and holding the successive analog components or values, after the oscillations have died out. Thus, smoother analog video signals are produced at the output of the sample and hold circuit 158.

The analog difference video signals at the output of the sample and hold circuit 158 are amplified by a buffer amplifier 159 having its output connected to the television display device or monitor 28. Thus, the television monitor 28 produces a continuous series of visible difference images, representing the difference between the current X-ray image and the integrated mask X-ray image which existed during the mask time interval. The subtraction of the mask image cancels out the image elements due to bone and soft tissue, so that the remaining difference image elements represent primarily the X-ray contrast medium, which was not present in the mask image, but is present in the images produced subsequent to the introduction of the contrast medium into the subject 12.

In the difference images displayed by the television monitor 28, the movement of the X-ray contrast medium in the heart and circulatory system of the subject is clearly visible. Thus, abnormalities in the functioning of the heart are rendered visible. If the second and third memory system 22 and 23 are operated so as to integrate the video signals over four television fields, the television monitor 28 will produce 15 different images per second, based on a television field frequency of 60 Hertz. Each image is produced four times before the next image is produced. The production of 15 images per second is sufficient to show the action of the heart clearly for accurate diagnosis of abnormal conditions.

If desired, the analog difference video signals from the output of the buffer amplifier 159 may also be supplied to a video disc recorder 162, so that the video signals can be recorded and played back repeatedly through the monitor 28.

If desired, a digital video disc recorder 162 may be employed, for recording the digital difference video signals at the output of the enhance circuit 156, or the raw digital video signals from the line 86. If the digital difference video signals are recorded by the digital disc recorder 162, the output of the recorder can subsequently be connected to the input of the DA converter, so that the recorded signals can be repeatedly displayed on the television display device 28. If the raw digital video signals are recorded, they can be subsequently reprocessed by connecting the output of the digital video disc recorder 162 to the line 86, so that the raw digital video signals will again be supplied to the inputs of the memory systems 21, 22 and 23. If desired, the memory systems 21, 22 and 23 can be readjusted to change the processing of the digital video signals. For example, the integrating time intervals of the memory systems 21, 22 and 23 can be changed by changing the timing pulses supplied by the system logic 32. It is also possible to change any of the constants $K_1$, $K_2$ and $K_3$ or the coefficients $A_1$, $A_2$ and $A_3$, or both.

In some cases, it may be desired to dispense with any integration of the digital video signals in the second and third memory systems 22 and 23. This can be accomplished by readjusting the system logic 32 so as to supply timing or gating pulses to the second and third memory systems 22 and 23, corresponding to a single television field. With this adjustment, the new data input registers 90b and c will transmit new data during alternate television fields. For example, during odd numbered television fields, the digital video signals from the line 86 will be transmitted through the input register 90b to the second memory system 22. This data, for a single television field, will be stored in the second memory 104b. During the even numbered television fields, the digital video signals stored in the second memory system 22 will be supplied through the electronic switch 146b to the subtraction circuit 142a. During such even numbered television fields, the raw digital video signals from the line 86 will be transmitted through the new data input register 90c to the third memory system 23 and will be stored therein. This stored data will be transmitted through the electronic switch 146c to the subtraction circuit 142a during the next odd numbered television field.

When the X-ray system 10 is thus adjusted for no integration in the second and third memory systems 22 and 23, the unintegrated digital video signals are supplied during each television field to the add input 144a of the subtraction circuit 142a, the unintegrated digital video signals being derived during alternate television fields from the second and third memory systems 22 and 23. During each television field, the integrated mask digital video signals from the first memory system 21 are subtracted from the unintegrated digital video systems as currently supplied to the subtraction circuit 142a. Thus, during each television field, the subtraction circuit 142a produces a new set of digital difference video signals. Accordingly, a new difference image is produced by the television display device 28 during each television field. For a television field frequency of 60 Hertz, the display device 28 produces sixty different difference images per second. However, for this mode of operation, there is no integration of the current digital video signals to improve the signal to noise ratio. Consequently, the difference video signals and the difference images contain a greater proportion of noise than when the current digital video signals are integrated over a few television fields.

The X-ray apparatus 10 can be simplified if there is never to be any integration of the current digital video signals. In that case, the second and third memories 104b and c are not needed. The third memory system 23 can be eliminated entirely. In the second memory system 22 it generally is desirable to retain the addition circuit 128b and the multiplication circuit 134b, so that the constant $K_2$ and the coefficient $A_2$ can be impressed upon the digital video signals. The current digital video signals from the line 86 can then be supplied directly to the input 126b of the addition circuit 128b.

For this simplified modification, the first memory system 21 is still needed to integrate the digital video signals during the mask time interval. The thirteen-ten multiplexer 124a may be readjusted to provide a thirteen-eight multiplexer, to develop an eight bit output, to match the eight bits of the raw digital video signals. In this simplified modification, the components 90b-124b of the second channel 22 are not needed and can be omitted. The output 138b of the second channel 22 is connected directly to the add input 144a of the subtraction circuit 142a, so that the electronic switches 146b and c are not needed.

As shown in FIG. 1, it is advantageous to employ an X-ray filter 164 in the path of the X-rays from the source 14, to increase the contrast produced by the X-ray contrast medium. When the contrast medium is in the form of a composition containing iodine, the X-ray filter 144 preferably contains samarium or cerium, or any other suitable element having a K-shell absorption edge in the range from 40 through 60 k.e.v. The use of such a filter material increases the visualization of iodine in the X-ray image. This result is caused primarily by the interplay between the K-edge absorption characteristics of iodine and the filter material.

In the X-ray apparatus of FIGS. 1 and 2, the video disc recorder 160 can also be employed to record the raw analog video signals. For this purpose, the video disc recorder is connected to the output line 76 for the buffer amplifier 74, as indicated in FIG. 1. After each run, the analog video signals can be played back into the line 76 and reprocessed through the AD converter 20, the memory system 21, 22 and 23, the subtraction means 24, the DA converter 26 and the television display device 28. For reprocessing, the memory systems 21, 22 and 23 can be adjusted differently than in the original run.

Similarly, the raw digital video signals on the line 86 can be recorded on the digital disc recorder 162. After each run, the recorded digital video signals can be played back into the line 86 and reprocessed.

During reprocessing, the mask time interval can be changed, as desired. In fact, any desired television fields during the run can be selected as the mask time interval, so that the digital video signals from these television fields can be integrated and stored in the first memory system 21. Instead of using the initial television fields to form the mask, it is possible to use television fields at a later time during the run, or even toward the end of the run.

By thus reprocessing the recorded video signals, various portions of the circulatory system, with the X-ray contrast medium therein, can sometimes be visualized even more clearly than in the original run.

FIG. 3 illustrates the manner in which the control means or system logic 32 controls the three memories 21, 22 and 23 and the subtraction means 24. During the mask time interval, the system logic supplies control signals which cause the first memory 21 to integrate the digital video signals for the duration of the mask time interval. The second and third memories 22 and 23 may be inactive during the mask time interval.

The duration of the mask time interval may be selected, as desired. For example, the mask time interval may extend for 31 television fields. This mask time interval has been employed successfully for numerous experiments, because the first memory system 21 happened to have an integrating storage capacity corresponding to the digital video signals from 31 television fields. However, it will be understood that the mask time interval may be varied over a wide range, certainly from one through sixty television fields or even considerably longer. The mask time interval of thirty-one television fields has been employed successfully for heart motion studies, even though this time interval is somewhat less than the typical duration of a complete cardiac cycle. If desired, the mask time interval may be established by control signals from the electrocardiographic signal source 30, so that the mask time interval will be synchronized with a complete cardiac cycle. On the other hand, the mask time interval may simply be timed to correspond with a particular number of television fields.

Following the mask time interval, the first image is stored and preferably integrated in the second memory system 22. Thus, the system logic 32 produces control signals which cause the second memory system 22 to integrate the incoming digital video signals. The interval of storage and integration usually corresponds to a few television fields, but is subject to wide variation, as desired, certainly from one to sixty television fields. For example, a storage and integrating interval of four television fields has been successfully employed in many experiments. This interval results in the production of fifteen difference images per second. This image rate produces good motion pictures which are useful for analysis of the motion of the heart. The integration of each image over several television fields improves the signal-to-noise ratio.

During the interval when the second memory system 22 is integrating the first image, the first memory system 21 is recirculating the integrated digital video signals for the mask. The third memory system 23 may be inactive during this interval.

During the next interval, the system logic 32 provides control signals which cause the third memory 23 to store and preferably integrate the digital video signals corresponding to the second image. At the same time, the system logic 32 produces control signals which cause the subtraction system 24 to subtract the integrated mask signals, derived from the output of the first memory system 21, from the first integrated image signals, derived from the second memory system 22. The first integrated image signals are directed to the add input 144a of the subtraction unit 142a, while the integrated mask signals are directed to the subtract input 140a of the subtraction unit 142a. The display 28 shows the first difference image, corresponding to the first image signals minus the mask signals.

During the next time interval, the system logic 32 produces control signals which cause the second memory 22 to integrate the incoming digital video signals for the third image. Here again, the integrating interval is usually a few television fields, such as four fields, for example. During this interval, the system logic 32 provides control signals which cause the second image output signals from the third memory 23 to be directed to the add input of the subtraction unit 142. At the same time, the mask output signals from the first memory 21 are directed to the subtract input of the subtraction circuit 142a. Accordingly, the display 28 shows a second difference image corresponding to the second image signals minus the mask signals.

This cycle is repeated as long as desired. The second and third memories 22 and 23 alternately integrate the incoming digital video signals, and then supply the integrated image signals to the add input of the subtraction unit 142a. A continuous display of difference images is thus maintained on the monitor 28.

Many variations of this mask mode procedure are possible. For example, for various abdominal X-ray studies, a modified procedure has been employed which produces a series of difference images resembling a slide show. In this modified method, the digital video signals are initially integrated to produce integrated mask signals. The mask integrating interval may be about thirty television fields, for example. Then, for the modified method, the system logic 32 produces a waiting period of perhaps 120 television fields, for example, during which the second and third memory systems 22 and 23 are inactive, while the first memory system 21 recirculates the integrated mask signals. The system logic 32 then causes the second memory system 22 to integrate the incoming digital video signals for a few television fields, to produce the first integrated image signals. Next, the system logic 32 produces another waiting interval, during which the integrated mask signals are subtracted from the first image signals to produce the first difference image. After the second waiting interval, the system logic 32 causes the third memory 23 to integrate the incoming digital video signals for a few television fields to produce the second integrated image signal. Another waiting interval is then produced, during which the integrated mask signals are subtracted from the second image signals to produce a second difference image. This procedure may be repeated to produce any desired number of difference images.

This modified method produces a series of difference images which are changed periodically after relatively long waiting intervals, such as 120 television fields. It will be understood that the waiting interval may be changed, as desired. The series of difference images will show the movement of a contrast medium through the field of view. This modified method is particularly valuable when the movement of the contrast medium is relatively slow, as in certain abdominal X-ray studies, for example.

For a modified method of this kind, the X-ray source 14 may be pulsed, so that X-rays will be produced only when they are needed, and not during the waiting intervals between the image integrating intervals. Thus, the exposure of the patient to X-rays is minimized.

The X-ray source 14 may be pulsed by a pulsed power supply 170, as shown in FIG. 1, which is controlled by control pulses or signals supplied by the system logic 32 over a signal line 172. The pulsed high voltage from the power supply 170 is delivered along a line 174 to the X-ray source 14.

FIG. 4 illustrates a modified X-ray apparatus 180 which is a modification of the X-ray apparatus 10 of FIGS. 1–3 and is a further illustrative embodiment of the generic invention. FIG. 4 represents a modified method which is appropriately called time interval differencing. By this modified method, visible difference images are produced in a different yet related manner, with respect to the mask mode represented by FIGS. 1–3.

In the time interval differencing method of FIG. 4, digital video signals may be derived from the X-ray image, in the same manner as in the mask mode of FIGS. 1–3. However, the digital video signals are integrated over a series of successive time intervals corresponding with a plurality of television fields. In this way, a series of sets of integrated digital video signals are produced. Preferably, three successive sets of integrated digital video signals are produced in rotation. Generally, the successive sets of integrated digital video signals are integrated over time intervals which are approximately equal, on the order of four television fields. The principal purpose of the integration is to improve the signal-to-noise ratio. The interval of integration may be varied over a wide range, as desired, from two to five television fields, at least, for example, or considerably longer, if desired.

In the time interval differencing method of FIG. 4, successive subtractions are performed in rotation between each set of integrated digital video signals, so as to produce a series of successive digital difference video signals. As before, the digital difference video signals are converted into analog difference video signals which are employed to produce a visible diplay of television difference images, representing the changes in the X-ray image between the successive time intervals.

As previously indicated, it is preferred to produce three successive sets of integrated digital video signals in rotation. In this preferred version of time interval differencing, the first set of integrated digital video signals is subtracted from the second set, the second set from the third, the third from the first, and so forth. This method of time interval differencing has the advantage that a continuous display of television difference images can readily be produced.

FIG. 4 illustrates apparatus modifications which are needed in the apparatus of FIG. 2, in order to carry out time interval differencing. Thus, FIG. 4 illustrates modified electronic switching means 182, to replace the electronic switches 146a and b of FIG. 2. The electronic switching means or matrix 182 of FIG. 4 is connected between the three output lines 138a, b and c and the input lines 140a and 144a of the subtraction circuit 142a. It will be recalled from the previous description that the output lines 138a, b and c are connected to the outputs of the three memory systems 21, 22 and 23.

The electronic switching matrix 182 of FIG. 4 comprises three electronic switches 184a, b and c which are connected between the respective output lines 138a, b and c and the add input 144a of the subtraction circuit 142a. In addition, the electronic switching matrix 182 comprises three electronic switches 186a, b and c which are connected between the output lines 138a, b and c and the subtraction input 140a of the subtraction circuit 142a. The electronic switches 184a, b and c are activated so as to transmit signals in rotation by timing or control pulses supplied from the system logic 32 over gate lines 188a, b and c, respectively. The control pulses supplied over the gate lines 188a, b and c are also employed to activate the electronic switches 186a, b and c, but the sequence is offset or staggered by one step. Thus, the second gate line 188b is connected to the first electronic switch 186a, associated with the first output line 138a. The third gate line 188c is connected to the second electronic switch 186b. The first gate line 188a is connected to the third electronic switch 186c.

In describing the operation of the apparatus of FIG. 4, it will be assumed for clarity that the integrating interval of each memory system is four television fields, although the integrating interval may be varied, as desired. The three memory systems 21, 22 and 23 may remain the same as described in connection with FIG. 2, except that the control signals supplied by the system logic 32 are timed so that the three memory systems 21, 22 and 23 integrate the digital video signals from the input line 86 for successive intervals of four television fields. Thus, for the first four television fields, the first memory system 21 is supplied with new digital video signals by the new data input register 90a. After the first four television fields, the register 90a is shut down by its gating pulses from the system logic 32. For the next eight television fields, the integrated and stored digital video signals in the first memory system 21 simply recirculate, and thus are available for transmission to the subtraction circuit 142a by the electronic switches 184a and 186a. During television fields 5–8, the first integrated digital video signals are transmitted by the electronic switch 184a to the add input 144a of the subtraction circuit 142a. During television fields 9–12, the first integrated digital video signals are supplied by the electronic switch 186a to the subtract input 140a of the subtraction circuit 142a.

During television fields 13–16, the new data input register 90a of the first memory system 21 is again activated, so that the new digital video signals are again integrated in the the first memory system 21. During television field 13, the previously stored data in the first memory system 21 is not recirculated, and thus is cancelled. This is easily accomplished by timing the control pulses from the system logic 32 so as to shut down the recirculation register 110a during television field 13. The register 110a is again activated during television fields 14–16, and remains activated for eight television fields thereafter.

For television fields 5–8, constituting the second set of four fields, the new digital video signals are integrated and stored in the second memory system 22. During the next eight fields 9–16, the new data input register 90b is shut down, so that the integrated and stored digital video signals are circulated in the second memory system 22. During television fields 9–12, the second integrated digital video signals are transmitted to the add input 144a of the subtraction circuit 142a by the electronic switch 184b. During television fields 13–16, the second integrated digital video signals are tansmitted to the subtract input 140a of the substraction circuit 142a by the electronic switch 186b.

This cycle, lasting twelve television fields, is repeated during the next twelve television fields and each subsequent interval of twelve television fields. During the first field of each twelve-field cycle, the data stored in the second memory system 22 is not recirculated and thus is discarded, so that only the new digital video signals are integrated.

The third memory system 20 also goes through successive twelve-field cycles. During the first four fields 9–12, the new digital video signals are admitted through the new data input register 90c and are integrated and stored in the third memory system 23. During the next eight television fields 13–20, the input register 90c is shut down by its control signals from the system logic 32, but the stored digital video signals are recirculated. During television fields 13–16, the third integrated digital video signals are transmitted through the electronic switch 184c to the add input 144a of the subtraction circuit 142a. During television frames 17–20, the third integrated digital video signals are transmitted through the electronic switch 186c to the subtract input 140a of the subtraction circuit 142a. This twelve-field cycle is repeated during each subsequent interval of twelve television fields. During the first field of each cycle, the previously integrated and stored data is not recycled and thus is discarded.

After the first eight television fields, during which the first and second memory systems 21 and 22 are being loaded with integrated digital video signals, the entire apparatus represented by FIG. 4 goes through a series of successive twelve-field subtraction cycles. During television fields 9–12, the first integrated digital video signals stored in the first memory system 21 are subtracted from the second integrated digital video signals stored in the second memory system 22, to produce difference video signals which are displayed on the television display device 28. A difference image is thus produced, in which the unchanging image elements are cancelled out. The difference image represents the differences or changes in the X-ray image between the two successive time intervals. A difference image is displayed four times during television fields 9–12.

During television fields 13–16, the second integrated digital video signals from the second memory system 22 are subtracted from the third integrated digital video signals from the third memory system 23, to produce another set of digital difference video signals. A corresponding difference image is displayed by the television display device 28. This image is displayed four times during television fields 13–16. During television fields 17–20, the third integrated digital video signals from the third memory system 23 are subtracted from the first integrated digital video signals from the first memory system 21, to produce a third set of digital difference video signals. A corresponding difference image is displayed four times by the television display device 28 during television fields 17–20. The twelve-field subtraction cycle is then repeated during each subsequent twelve-field cycle.

The apparatus 180 represented by FIG. 4 thus produces a continuous series of difference images, representing the progressive changes in the X-ray image. The difference images displayed by the display device 28 represent approximately the first derivative of the X-ray image. In the human or other anatomical subject 12 of FIG. 1, the image elements due to bone and soft tissue are largely unchanging, and thus are largely cancelled out in the difference images. However, any movement, such as heart movement, is preserved in the difference images. Thus, time interval differencing, as represented by FIG. 4, is advantageous for its ability to visualize heart movement, without being obscured by unchanging bone and soft tissue.

While heart movement can be visualized without the use of an X-ray contrast medium, it is often advantageous to increase the degree of visualization by introducing an X-ray contrast medium into the anatomical subject 12, with a timing such that the contrast medium becomes operative during the time interval differencing. It is not necessary to insert a catheter to introduce the contrast medium near the heart. Instead, the contrast medium can simply be injected into one or more veins in the arms or legs of the subject. The peripheral injection of the X-ray contrast medium eliminates the hazard which is associated with the insertion of a catheter into the circulatory system.

The X-ray contrast medium may take the form of a composition containing iodine. In that case, it is advantageous to employ an X-ray filter containing cerium in the path of the X-rays from the source 14. The cerium filter increases the contrast produced by the iodine composition, due to the interplay between the K-edge absorption characteristics of cerium and iodine.

In time interval differencing, as represented by FIG. 4, each stored set of digital video signals serves as a mask for a subsequent set of stored video signals. Accordingly, there is a general relationship between time interval differencing, as represented by FIG. 4, and the mask mode, as represented by FIGS. 1 and 2. However, in time interval differencing, the mask is updated during each successive integrating interval. In the mask mode, the same set of integrated digital video signals is employed as a mask during each succeeding interval.

It will be understood that the integrating interval in time interval differencing can be varied from two television fields upwardly. Moreover, time interval differencing can be employed without integration. In that case, each of the three memory systems 21–23 is simply employed to store the digital video signals for a single television field. Each stored set of digital video signals is then substracted from the next set. However, in the absence of integration, the resulting difference images will suffer from a lower signal to noise ratio.

Any known or suitable X-ray contrast medium may be employed in connection with the disclosed methods. Alternatively, the disclosed methods may be employed without using any contrast medium.

X-ray filtration may be employed, with or without the use of a contrast medium. The X-ray filter may advantageously contain samarium or cerium when a contrast medium containing iodine is used. Instead of samarium or cerium, the X-ray filter may contain any other suitable element having a k-shell absorption edge between 40 and 60 k.e.v, both inclusive. However, the X-ray filter may be of any known or suitable composition, adapted to enhance the visibility of the physiological features to be examined.

The subject matter of FIG. 4 is disclosed and claimed in the copening application of Charles A. Mistretta, Robert A. Kruger and Theodore L. Houk.

Figure 5:
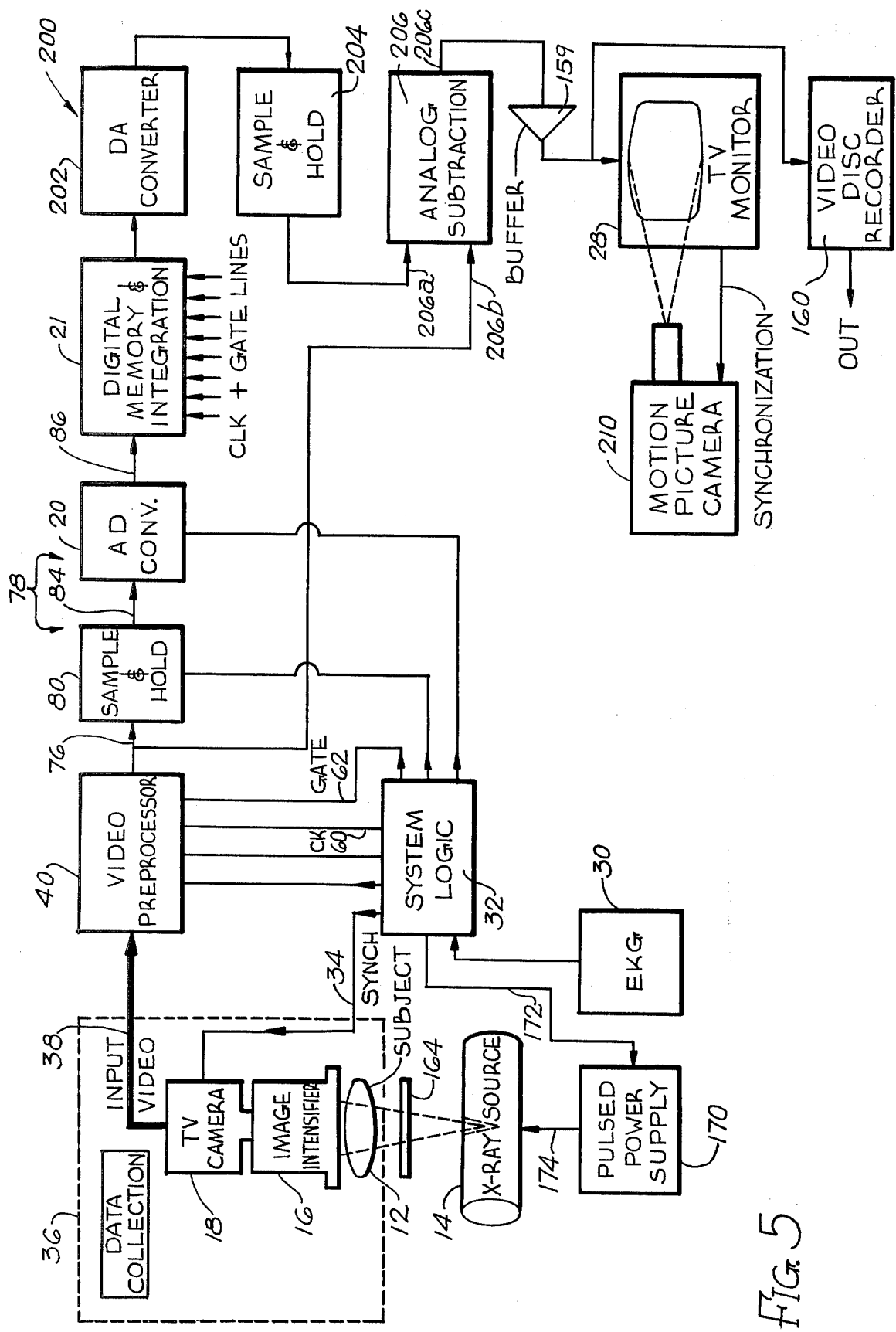
FIG. 5 is a schematic block diagram of another modified apparatus utilizing analog subtraction.

FIG. 5 illustrates another modified mask mode apparatus 200 which is similar in many ways to the apparatus 10 of FIGS. 1 and 2, but utilizes only a single memory system, which may be the same as the first memory system 21 of FIG. 2, and is so designated in FIG. 5. The memory system 21 is employed in substantially the same manner as in the system 10 of FIG. 1, to store and integrate a set of digital mask video signals, representing an integrated mask image. The digital mask video signals are then converted into analog signals and are subtracted in real time from the currently produced incoming analog video signals to produce analog difference video signals, which may be supplied to the video display device or monitor 28 or to the video disc recorder 160, as before. More specifically, the modified mask mode apparatus 200 of FIG. 5 may employ most of the same components as in the system 10 of FIGS. 1 and 2. Thus, the data collection means 36, the video preprocessor 40, the digitizer 78 and the memory system 21 may be the same as described in connection with FIGS. 1 and 2. As before, the digitizer 78 converts the analog video signals, supplied by the output line 76 from the video processor 40, into corresponding digital video signals, which are supplied over the line 86 from the output of the analog-to-digital converter 20 to the input of the digital memory system 21.

As previously described, the digital memory system 21 stores and integrates the digital video signal 5 over a mask time interval. The integrated mask video signals 5 from the output of the memory system 21 are then supplied to the input of a digital-to-analog converter 202, which may be substantially similar to the DA converter 26 of FIG. 2. The DA converter 202 of FIG. 5 converts the digital mask video signals into corresponding analog video signals, which preferably are transmitted through a sample and hold circuit 204 to one of the inputs of an analog subtraction circuit 206, preferably the subtraction input 206a. The other input 206b of the subtraction circuit 206 is supplied with the currently produced incoming analog video signals, preferably from the output line 76 of the video preprocessor 40.

The analog subtraction circuit 206 subtracts the analog mask video signals at the subtract input 206a from the currently produced incoming analog video signals 20 at the add input 206b, so as to produce video difference signals at the output line 206c. These video difference signals are supplied to the input of the television display device or monitor 28, preferably through the buffer amplifier 159, as in the system of FIGS. 1 and 2. The output of the amplifier 159 may also be supplied to the input of the video disc recorder 160, as before.

With the apparatus 200 of FIG. 5, the analog video difference signals are not electronically integrated, but a form of integration may be produced by providing a motion picture camera 210 to photograph the image produced by the television display device 28. The motion picture camera 210 may be synchronized with the television monitor 28, so that a plurality of television fields are photographed during each frame produced by the motion picture camera 210. For example, four television fields may be photographed on each motion picture frame. This procedure has the effect of producing motion pictures which are integrated over four television fields. In this way, the signal-to-noise ratio of the motion pictures is improved.

In the method carried out by the modified apparatus 200 of FIG. 5, an X-ray image is produced by directing X-rays from the X-ray source 14 through the anatomical subject 12, which may be a person or an animal. The X-ray image is converted into television fields by the image intensifier 16 and the TV camera 18. The television fields comprise a train or series of analog video signals, which are electronically processed by the video processor 40, as previously described. It will be recalled that such processing includes logarithmic amplification.

The preprocessed analog video signals are then transmitted through the sample and hold circuit 80 to the analog-to-digital converter 20, which converts the analog signals into digital video signals. During the mask time interval, the digital video signals are stored and integrated by the digital memory system 21, to produce digital integrated mask video signals. As previously described, the mask time interval normally comprises a plurality of successive television fields, preferably corresponding generally with at least one complete cardiac cycle of the anatomical subject 12, or a major fraction of one complete cardiac cycle. The mask time interval may be initiated and terminated by triggering signals from the electrocardiogram apparatus 30, or from blood pressure sensors. Alternatively, the mask time interval may be established as a particular number of television fields, such as 31, for example, corresponding roughly to one complete cardiac cycle. Subsequent to the mask time interval, the digital integrated mask video signals are supplied to the digital-to-analog converter 202, which reconverts the digital signals to analog integrated mask video signals. The analog subtraction circuit 206 then carries out an analog subtraction between the currently produced or ongoing analog video signals and the analog integrated mask video signals. Such integrated mask video signals represent the background of bone and soft tissue. Such background is cancelled out by the subtraction operation.

The analog video difference signals from the analog subtraction circuit 206 are supplied to the television monitor 28 through the buffer amplifier 159. The television monitor 28 converts the video difference signals to television difference images, which represent successive changes in the X-ray image, subsequent to the mask time interval.

It is preferred to inject or introduce an X-ray contrast medium into the anatomical subject 12, with a timing such that the contrast medium will not be operative during the mask time interval, but will be operative when the difference images are produced, subsequent to the mask time interval. It is preferred to inject an X-ray contrast medium containing iodine into a peripheral blood vessel of the anatomical subject 12, such as a vein in an arm or leg of the subject.

It has been found that the electronic subtraction of the integrated mask results in effective cancellation of the background image elements produced by bone and soft tissue, so that the visibility of the contrast medium is greatly enhanced. Such enhancement is so pronounced that it is possible to reduce the dosage of the contrast medium, and to inject the contrast medium peripherally, into a vein in an arm or leg, rather than inserting a catheter to carry the contrast medium directly to the heart, or to some other location of special interest in the circulatory system.

The system 200 of FIG. 5 has the advantage that the ongoing video signals and the video difference signals are handled by a channel which is purely analog in character, so that there is no loss of resolution due to digitizing of the video signals. Thus, the full analog resolution or fidelity of the analog channel is employed to handle and process the video signals and the video difference signals. Only the mask video signals are digitized for storage and integration.

The high resolution or fidelity of the analog channel preserves the high frequency components of the video signals, which carry the fine details of the television images. Thus, the fine details are maintained in the television difference images produced by the TV monitor 28.

The resolution of the integrated mask signals is limited by the digitizing process and also by the digital capacity of the memory system 21. In effect, this limited resolution produces a blurring of the mask represented by the integrated mask video signals. However, unexpectedly, it has been found that the subtraction of the somewhat blurred mask results in the production of high quality television difference images, in which the visibility of the X-ray contrast medium is greatly enhanced.

With the modified system 200 of FIG. 5, it is possible to increase the resolution of the basic television system, to take advantage of the full resolution of the analog channel, without any necessity for increasing the resolution of the digital channel, comprising the AD converter 20, the memory system 21, and the DA converter 202. For example, consider the case in which the digital memory 21 has a capacity of 256 television lines, each comprising 256 pixels, each represented by a 13 bit digital word. If desired, the resolution of the television system may be increased by increasing the line frequency to 1024 television lines in each television field. The pixel resolution may also be increased to correspond with at least 1024 pixels per line. This high level of resolution can be maintained by the analog channel, comprising the video preprocessor 40, the analog subtraction circuit 206, the buffer amplifier 159 and the television monitor 28. To accommodate the increased line frequency, the analog-to-digital converter 20 may be modified to include a line frequency conversion circuit. For example, the conversion circuit may be such that four successive television lines are integrated or averaged, as by summing the digital values of the corresponding pixels of the four lines, and then dividing each sum by four. The average pixel values are then stored in the digital memory system 21 and are integrated with the corresponding average pixel values from the successive television fields in the mask time interval.

The digital-to-analog converter 202 may be modified to reconvert the line frequency from 256 to 1024. For example, each of the stored and integrated television lines in the memory system 21 may be converted four times in rapid succession to analog form.

Unexpectedly, it has been found to be highly advantageous to integrate the mask video signals for a large number of television fields, corresponding generally to one complete cardiac cycle, or a major fraction thereof. Of course, during the cardiac cycle, movement of the heart and blood vessels takes place, due to the beating of the heart and the pulsing of the blood vessels. This movement effectively causes blurring of the mask represented by the integrated mask video signals. Nevertheless, it has been found that the subtraction of this somewhat blurred mask from the ongoing video signals results in the production of high quality television difference images. In such difference images, the fine detail is derived predominantly from the ongoing video signals, rather than from the integrated mask signals. The general background of soft tissue and bone, represented by the blurred mask signals, is cancelled out in the television difference images.

The mask time interval is preferably on the order of at least one complete cardiac cycle of the anatomical subject. Thus, for example, the mask time interval may comprise a particular number of television fields, having a total length on the order of one complete cardiac cycle. By way of specific example, a mask time interval of 31 television fields has been employed very successfully to produce high quality television difference images. An alternative method is to employ electrocardiographic signals, or blood pressure signals, to synchronize the mask time interval with one or more complete cardiac cycles of the subject.

I claim:

1. A method of producing visible difference images derived from an X-ray image of an anatomical subject, comprising the steps of directing X-rays through the anatomical subject for producing an X-ray image,
converting said X-ray image into television fields comprising trains of analog video signals,
converting said analog video signals into digital video signals,
producing integrated digital video signals by integrating said digital video signals over a predetermined time interval corresponding to a plurality of successive television fields,
producing digital difference video signals by performing a subtraction between the digital video signals for a selected time different from said time interval and the corresponding integrated digital video signals,
converting said digital difference video signals into analog difference video signals,
and converting said analog difference video signals into visible television difference images representing changes in the X-ray image.

2. A method according to claim 1, in which said time interval is established to be at least on the order of one complete cardiac cycle of the subject.

3. A method according to claim 1, including the step of introducing an X-ray contrast medium into the subject with a timing such that said contrast medium is differently operative at said selected time and during said time interval.

4. A method according to claim 1, including the step of introducing an X-ray contrast medium into the subject with a timing such that the contrast medium is not operative during said time interval but is operative during the digital video signals which are involved in said subtraction.

5. A method according to claim 1, including the step of logarithmically amplifying said analog video signals prior to the conversion to digital signals.

6. A method according to claim 1, in which said analog video signals are converted directly into said digital video signals in real time without any intervening analog storage.

7. A method according to claim 1, in which said analog video signals are converted directly into said digital video signals in real time without any intervening analog storage, said integrated digital video signals, said digital difference video signals, said analog difference video signals and said visible television difference images being produced in real time.

8. A method of producing visible difference images derived from an X-ray image of an anatomical subject, comprising the steps of directing X-rays through the anatomical subject for producing an X-ray image,
converting said X-ray image into television fields comprising trains of analog video signals,
converting said analog video signals into digital video signals,
producing first integrated digital video signals by integrating said digital video signals over a first predetermined time interval corresponding to a plurality of successive television fields,
producing second integrated digital video signals by integrating said digital video signals over a second predetermined time interval subsequent to said first time interval and corresponding to a plurality of successive television fields,
producing digital difference video signals by performing a subtraction between said second integrated digital video signals and said first integrated digital video signals, converting said digital difference video signals into analog difference video signals, and converting said analog difference video signals into visible television difference images representing the changes in the X-ray image subsequent to said first time interval.

9. A method according to claim 8, in which said first time interval is substantially greater in length than said second time interval.

10. A method according to claim 8, in which said first time interval is established to be at least on the order of one complete cardiac cycle of the subject, said first time interval being substantially greater in length than said second time interval.

11. A method according to claim 8, in which said first time interval is established to be on the order of one complete cardiac cycle of the subject, said second time interval being on the order of four television fields.

12. A method according to claim 8, including the step of introducing an X-ray contrast medium into the subject with a timing such that the contrast medium is not operative during the first time interval but is operative during the second time interval.

13. A method according to claim 8, including the step of logarithmically amplifying the analog video signals prior to the conversion to digital signals.

14. A method of producing visible difference images derived from an X-ray image of an anatomical subject, comprising the steps of directing X-rays through the anatomical subject for producing an X-ray image, converting said X-ray image into television fields comprising trains of analog video signals, converting said analog video signals into digital video signals, producing integrated mask digital video signals by integrating said digital video signals over a predetermined number of successive television fields for a mask time interval, subtracting the integrated mask digital video signals from corresponding digital video signals of television fields subsequent to said mask time interval and thereby producing digital difference video signals, converting said digital difference video signals into analog difference video signals, and converting said analog difference video signals into a series of visible television difference images representing changes in the X-ray image subsequent to said mask time interval.

15. A method according to claim 14, including the step of introducing an X-ray contrast medium into the subject at a time to be operative subsequent to the mask time interval.

16. A method according to claim 14, including the step of establishing the mask time interval to be at least on the order of one complete cardiac cycle of the subject.

17. A method according to claim 14, including the step of logarithmically amplifying the analog video signals prior to the conversion to digital signals.

18. A method according to claim 14, including the step of introducing an X-ray contrast medium into a peripheral blood vessel of the subject with a timing such that said contrast medium appears in the X-ray image subsequent to said mask time interval.

19. A method according to claim 14, including the step of integrating the digital video signals subsequent to said mask time interval over a series of successive second time intervals corresponding to a plurality of successive television fields, and then performing said subtraction step by subtracting the integrated mask digital signals from each successive set of digital signals integrated over the successive second time intervals.

20. A method according to claim 19, in which each second time interval is on the order of four television fields.

21. A method according to claim 14, including the step of introducing an X-ray contrast medium into the subject to be operative subsequent to the mask time interval, and the step of producing filtration of the X-rays to enhance the visibility of the X-ray contrast medium.

22. A method according to claim 21, utilizing the X-ray contrast medium containing iodine.

23. A method according to claim 22, in which the X-ray filtration is produced with an X-ray filter medium containing cerium to enhance the visibility of the iodine.

24. A method according to claim 22, in which the X-ray filtration is produced with an X-ray filter medium containing an element having a k-shell absorption edge in the range from 40 through 60 k.e.v. to enhance the visibility of the iodine.

25. A method according to claim 22, in which the X-ray filtration is produced with an X-ray filter medium containing samarium to enhance the visibility of the iodine.

26. Diagnostic anatomical X-ray apparatus, comprising means including an X-ray source for producing an anatomical X-ray image of a subject, television means for converting said X-ray image into a series of television fields comprising trains of analog video signals, an analog-to-digital converter for converting said analog video signals into corresponding digital video signals, a digital memory system including means for storing and integrating said digital video signals over a predetermined time interval corresponding with a plurality of successive television fields, subtracting means for producing digital difference video signals by performing a subtraction between the digital video signals subsequent to said time interval and the corresponding integrated digital video signals stored in said memory system, a digital-to-analog converter for converting said digital difference video signals into analog difference video signals, and means including a television display device for producing visible difference images corresponding to said analog difference video signals and representing changes in the anatomical X-ray image subsequent to said time interval.

27. Diagnostic anatomical X-ray apparatus according to claim 26,
including means for establishing said time interval to be at least on the order of one complete cardiac cycle of the subject.

28. Diagnostic anatomical X-ray apparatus according to claim 26,
including electrocardiographic means for establishing said time interval to correspond with at least one complete cardiac cycle of the subject.

29. Diagnostic anatomical X-ray apparatus according to claim 26,
including a logarithmic amplifier for logarithmically amplifying said analog video signals for presentation to said analog-to-digital converter.

30. Apparatus according to claim 26,
in which said analog-to-digital converter is connected directly to said television means without any intervening storage for directly converting said analog video signals into said digital video signals in real time.

31. Diagnostic anatomical X-ray apparatus, comprising
means including an X-ray source for producing an anatomical X-ray image of a subject,
television means for converting said X-ray image into a series of television fields comprising trains of analog video signals,
an analog-to-digital converter for converting said analog video signals into corresponding digital video signals,
a first digital memory system including means for storing and integrating said digital video signals over a first predetermined time interval corresponding with a plurality of successive television fields to produce first integrated digital video signals,
a second digital memory system including means for integrating and storing said digital video signals over a second predetermined time interval subsequent to said first time interval and corresponding with a plurality of successive television fields to produce second integrated digital video signals,
subtracting means for producing digital difference video signals by performing a subtraction between said second integrated digital video signals and said first integrated digital video signals,
a digital-to-analog converter for converting said digital difference video signals into analog difference video signals,
and means including a television display device for producing visible difference images corresponding to said analog difference video signals and representing changes in the anatomical X-ray image between said first and second time intervals.

32. Diagnostic anatomical X-ray apparatus according to claim 31,
including means for establishing said first time interval to be substantially greater in length than said second time interval.

33. Diagnostic anatomical X-ray apparatus according to claim 31,
including means for establishing said first time interval to be at least on the order of one cardiac cycle of the subject,
and means for establishing said second time interval to be substantially shorter in length than said first time interval.

34. Diagnostic anatomical X-ray apparatus according to claim 31,
including means for establishing said first time interval to be at least on the order of one complete cardiac cycle of the subject,
and means for establishing said second time interval to be on the order of four television fields.

35. Diagnostic anatomical X-ray apparatus, comprising
means including an X-ray source for producing an anatomical X-ray image of a subject,
television means for converting said X-ray image into a series of television fields comprising trains of analog video signals,
an analog-to-digital converter for converting said analog video signals into corresponding digital video signals,
a mask producing memory system for storing and integrating said digital video signals over a predetermined mask time interval,
said memory system comprising a digital memory having a capacity corresponding to at least one television field and integrating means for causing said digital memory to integrate said digital video signals over a predetermined number of successive television fields for said mask time interval,
subtracting means for producing digital difference video signals by performing a subtraction between the digital video signals subsequent to said mask time interval and the corresponding integrated digital video signals stored in said memory,
a digital-to-analog converter for converting said digital difference video signals into analog difference video signals,
and means including a television display device for producing visible difference images corresponding to said analog difference video signals and representing changes in the anatomical X-ray image taking place subsequent to said mask time interval.

36. Diagnostic anatomical X-ray apparatus according to claim 35,
including second and third memory systems connected to said analog-to-digital converter for integrating and storing the incoming digital video signals subsequent to said mask time interval for a series of second time intervals,
and means for supplying the most recently integrated and stored digital video signals to said subtracting means whereby said subtracting means performs a subtraction between such most recently integrated and stored digital video signals integrated over the immediately previous second time interval and the digital video signals integrated over said mask time interval to maintain a continuous display of difference images.

37. Diagnostic anatomical X-ray apparatus according to claim 35,
including electrocardiographic signal producing means connected to said mask producing memory system for synchronizing said mask time interval with at least one complete cardiac cycle of the subject.

38. Diagnostic anatomical X-ray apparatus according to claim 35,
comprising X-ray filtration means for filtering the X-rays from said source to enhance the visibility of a predetermined X-ray contrast medium.

39. Diagnostic anatomical X-ray apparatus according to claim 35,
comprising X-ray filtration means for filtering the X-rays from said source,
said X-ray filtration means containing cerium for enhancing the visibility of an X-ray contrast medium containing iodine.

40. Diagnostic anatomical X-ray apparatus according to claim 35,
including a logarithmic amplifier for logarithmically amplifying said analog video signals for presentation to said analog-to-digital converter.

41. Diagnostic anatomical X-ray apparatus according to claim 35,
comprising X-ray filtration means for filtering the X-rays from said source,
said X-ray filtration means containing an element having a k-shell absorption edge in the range from 40 through 60 k.e.v. for enhancing the visibility of an X-ray contrast medium containing iodine.

42. Diagnostic anatomical X-ray apparatus according to claim 35,
comprising X-ray filtration means for filtering the X-rays from said source,
said X-ray filtration means containing samarium for enhancing the visibility of an X-ray contrast medium containing iodine.

43. Diagnostic anatomical X-ray apparatus according to claim 35,
including additional memory means connected between said analog-to-digital converter and said subtracting means for integrating said digital video signals for a series of second predetermined time intervals subsequent to said mask time interval whereby said subtracting means performs a series of subtractions between the digital video signals integrated by said additional memory means over the successive second time intervals and the digital video signals integrated over said mask interval.

44. Diagnostic anatomical X-ray apparatus according to claim 43,
in which said additional memory means comprises means for integrating the incoming digital video signals over each successive second time interval,
means for successively storing the most recently integrated digital video signals,
and means for supplying the most recently stored digital video signals to said subtracting means for maintaining a continuous display of difference images.

45. Diagnostic anatomical X-ray apparatus according to claim 43, 'in which said additional memory means comprises second and third memory systems for successively integrating and storing the incoming digital video signals for the series of successive second time intervals,
and means for successively supplying the most recently stored digital video signals from said second and third memory systems to said subtracting means to maintain a continuous display of difference images.

46. Diagnostic anatomical X-ray apparatus according to claim 43,
including means for establishing each of said second time intervals so as to be on the order of four television fields.

47. Diagnostic anatomical X-ray apparatus according to claim 43,
comprising means for establishing each of said second time intervals to correspond with a plurality of complete television fields.

48. A method of producing visible difference images derived from an X-ray image of an anatomical subject, comprising
the steps of directing X-rays through the anatomical subject for producing an X-ray image,
converting said X-ray image into television fields comprising trains of video signals,
storing and integrating said video signals over a mask time interval corresponding to a plurality of successive television fields and thereby producing a set of stored and integrated video signals,
recovering said stored and integrated video signals from storage and thereby producing integrated video mask signals,
producing video difference signals by performing a subtraction between the mask video signals and the ongoing video signals outside the mask time interval, and
converting said video difference signals into visible television difference images representing the changes in the X-ray image subsequent to the mask time interval.

49. A method according to claim 43,
said video signals being produced in an analog form,
said analog video signals being converted into digital form for storage and integration.

50. A method according to claim 43,
said video signals being produced in an analog form,
the analog video signals being converted into digital form for storage and integration,
said video mask signals being reconverted to analog form,
said subtraction being carried out on an analog basis between the on-going analog video signals and the analog video mask signals.

51. A method according to claim 48,
said video signals being produced on an analog basis,
the analog video signals being converted into digital form for storage and integration and also for subtraction,
the subtraction being carried out digitally between the on-going digital video signals and the digital video mask signals to produce digital video difference signals which are then reconverted into analog video difference signals.

52. A method according to claim 48,
in which said mask time interval corresponds generally to at least on the order of one complete cardiac cycle of the anatomical subject.

53. A method according to claim 48,
in which said mask time interval corresponds generally to at least on the order of one complete cardiac cycle of the anatomical subject,
said video signals being produced in an analog form,
the analog video signals being converted into digital form for storage and integration to produce digital video mask signals,
the digital video mask signals being reconverted into analog form for analog subtraction between the on-going analog video signals and the analog video mask signals.

54. A method according to claim 48,
in which said mask time interval corresponds generally to at least on the order of one complete cardiac cycle of the anatomical subject,
said video signals being produced in an analog form,
the analog video signals being converted to digital form for storage, integration and subtraction to produce digital video difference signals,
the digital video difference signals being reconverted to analog video difference signals.

55. A method according to claim 48,
in which an X-ray contrast medium is injected into a peripheral blood vessel of the anatomical subject with a timing such that said X-ray contrast medium appears in the X-ray image subsequent to said mask time interval,
the visibility of the X-ray contrast medium being enhanced in the visible television difference images.

56. A method according to claim 48,
in which said mask time interval corresponds generally to at least on the order of one complete cardiac cycle of the anatomical subject,
an X-ray contrast medium being injected into a peripheral blood vessel of the anatomical subject with a timing such that said X-ray contrast medium appears in the X-ray image subsequent to said mask time interval,
the visibility of the X-ray contrast medium being enhanced in said visible television difference images.

57. A method according to claim 48,
including the step of producing motion picture frames of said visible television difference images with a timing such that each motion picture frame includes a plurality of television fields to improve the signal-to-noise ratio.

58. Diagnostic anatomical X-ray apparatus,
comprising means including an X-ray source for producing an anatomical X-ray image of a subject,
television means for converting said X-ray image into a series of television fields comprising trains of video signals,
a mask producing memory system for storing and integrating said video signals over a mask time interval corresponding generally to a plurality of successive television fields,
said memory system having a storage capacity corresponding to at least said mask time interval,
subtracting means for producing video difference signals by performing a subtraction between the on-going video signals outside said mask time interval and the stored and integrated video signals in said memory, and
means including a television display device for producing visible difference images corresponding to said video difference signals and representing changes in the anatomical X-ray image taking place outside said mask time interval.

59. Apparatus according to claim 58,
including means in said television means for producing said video signals in analog form,
an analog-to-digital converter for converting said analog video signals into corresponding digital video signals,
said memory system comprising a digital memory and digital integrating means for causing said digital memory to integrate the digital video signals for said mask time interval,
and a digital-to-analog converter for converting the integrated digital video signals into integrated analog mask video signals,
said subtracting means performing an analog subtraction between the on-going analog video signals and the analog mask video signals.

60. Apparatus according to claim 58,
including means in said television means for producing said video signals in analog form,
an analog-to-digital converter for converting the analog video signals into corresponding digital video signals,
said memory system comprising a digital memory and digital integrating means for causing the digital memory to integrate the digital video signals to produce digital video mask signals,
said subtracting means including means for producing a digital subtraction between the digital video signals and the digital mask video signals to produce digital video difference signals,
and a digital-to-analog converter for converting said digital video difference signals into analog video difference signals.

61. Apparatus according to claim 58,
including means for establishing the mask time interval to correspond generally with at least on the order of one complete cardiac cycle of the anatomical subject.

62. Apparatus according to claim 58,
including a motion picture camera for producing motion picture frames of said visible difference images with a timing such that each motion picture frame includes a plurality of television fields to improve the signal-to-noise ratio.

63. Diagnostic anatomical X-ray apparatus,
comprising means including an X-ray source for producing an anatomical X-ray image of a subject,
television means for converting said X-ray image into a series of television fields comprising trains of analog video signals,
an analog-to-digital converter connected directly to said television means for converting said analog video signals into corresponding digital video signals in real time,
a digital memory system including means for storing and integrating said digital video signals in real time over a predetermined time interval corresponding with a plurality of successive television fields,
subtracting means for producing digital difference video signals in real time by performing a subtraction in real time between the digital video signals subsequent to said time interval and the corresponding integrated digital video signals stored in said memory system,
a digital-to-analog converter for converting said digital difference video signals into analog difference video signals in real time,
and means including a television display device for producing visible difference images in real time and corresponding to said analog difference video signals, said visible difference images representing changes in the anatomical X-ray images subsequent to said time interval.

64. A method of producing visible difference images drived from an X-ray image of an anatomical subject,
comprising the steps of directing X-rays through the anatomical subject for producing an X-ray image,
converting said X-ray image into television fields comprising trains of analog video signals,
converting said analog video signals into corresponding digital video signals in real time for storage and integration,
storing and integrating said digital video signals in real time over a mask time interval corresponding to a plurality of successive television fields and thereby producing a set of stored and integrated digital video signals,
recovering said stored and integrated digital video signals from storage in real time and thereby producing integrated mask digital video signals,
converting said integrated mask digital video signals to corresponding integrated mask analog video signals,
producing video difference analog signals by performing a subtraction in real time between the integrated mask analog video signals and the ongoing analog video signals outside the mask time interval,
and converting said video difference analog signals in real time into visible television difference images representing the changes in the X-ray image subsequent to the mask time interval.

65. Diagnostic anatomical X-ray apparatus, comprising means including an X-ray source for producing an anatomical X-ray image of a subject,
television means for converting said X-ray image into a series of television fields comprising trains of analog video signals,
an analog-to-digital converter connected to said television means for converting said analog video signals into corresponding digital video signals in real time for storage and integration,
a digital memory system including means for storing and integrating said digital video signals in real time over a predetermined time interval corresponding with a plurality of successive television fields,
said memory system comprising a digital memory and digital integrating means for causing said digital memory to integrate the digital video signals for said mask time interval to produce integrated mask digital video signals,
a digital-to-analog converter for converting the integrated mask digital video signals into integrated mask analog video signals,
subtracting means for producing video difference signals by performing a subtraction in real time between the ongoing analog video signals outside said mask time interval and the integrated mask analog video signals,
and means including a television display device for producing visible difference images in real time and corresponding with said analog video difference signals,
said visible difference images representing changes in the anatomical X-ray image subsequent to said mask time interval.

* * * * *

UNITED STATES PATENT AND TRADEMARK OFFICE
CERTIFICATE OF CORRECTION

PATENT NO. : 4,204,225
DATED : May 20, 1980
INVENTOR(S) : Charles A. Mistretta

It is certified that error appears in the above-identified patent and that said Letters Patent are hereby corrected as shown below:

On the title page, under the heading "OTHER PUBLICATIONS",
column 1, 2nd to the last line, after "Acquisition" insert -- ", --  ;
      last line, after "Radiology" delete the quotation mark;

column 2, line 5, after "Densitometry" insert -- ", -- ;
      line 6, after "Processing" delete the quotation mark.

Column 7, line 49, after "110a" insert -- are --

Column 16, line 48, "tansmitted" should be -- transmitted --

Column 16, line 48, "substraction" should be -- subtraction --

Column 18, line 43, "copening" should be -- copending --

Column 19, line 50, "processor" should be -- preprocessor --

Column 22, line 8, "substraction" should be -- subtraction --

Column 31, line 5, "drived" should be -- derived --

Signed and Sealed this

Ninth Day of December 1980

[SEAL]

Attest:

SIDNEY A. DIAMOND

Attesting Officer      Commissioner of Patents and Trademarks